(12) United States Patent
Filipovic et al.

(10) Patent No.: US 9,207,715 B2
(45) Date of Patent: Dec. 8, 2015

(54) PERSONAL CLOUD WITH A PLURALITY OF MODULAR CAPABILITIES

(71) Applicant: Micro Mobio Corporation, Palo Alto, CA (US)

(72) Inventors: Zlatko Aurelio Filipovic, San Jose, CA (US); Weiping Wang, Palo Alto, CA (US); Adam James Wang, Palo Alto, CA (US)

(73) Assignee: Micro Mobio Corporation, Palo Alto, CA (US)

( * ) Notice: Subject to any disclaimer, the term of this patent is extended or adjusted under 35 U.S.C. 154(b) by 25 days.

(21) Appl. No.: 14/036,729

(22) Filed: Sep. 25, 2013

(65) Prior Publication Data

US 2014/0085815 A1    Mar. 27, 2014

Related U.S. Application Data

(63) Continuation-in-part of application No. 13/831,663, filed on Mar. 15, 2013, now Pat. No. 9,086,847.

(60) Provisional application No. 61/705,383, filed on Sep. 25, 2012.

(51) Int. Cl.
*G06F 1/16* (2006.01)
*H04B 1/3888* (2015.01)
*H04M 1/02* (2006.01)
*H04M 1/18* (2006.01)

(52) U.S. Cl.
CPC .............. *G06F 1/1633* (2013.01); *G06F 1/163* (2013.01); *G06F 1/1628* (2013.01); *G06F 1/1632* (2013.01); *G06F 1/1698* (2013.01); *H04B 1/3888* (2013.01); *H04M 1/0254* (2013.01); *H04M 1/185* (2013.01)

(58) Field of Classification Search
CPC ....................................................... G06F 1/1626
USPC ....................................................... 361/679.56
See application file for complete search history.

(56) References Cited

U.S. PATENT DOCUMENTS

| | | | |
|---|---|---|---|
| 6,442,018 B1 | 8/2002 | Dinkin | |
| 7,265,970 B2 * | 9/2007 | Jordan | 361/679.27 |
| 7,558,057 B1 * | 7/2009 | Naksen et al. | 361/679.56 |
| 7,743,999 B1 | 6/2010 | Griffin | |
| 8,035,577 B2 * | 10/2011 | Lafarre et al. | 345/55 |
| 8,328,055 B1 * | 12/2012 | Snyder | 224/197 |
| 8,605,421 B2 * | 12/2013 | Verschoor et al. | 361/679.3 |
| 8,896,992 B2 * | 11/2014 | Sherlock | 361/679.03 |
| 8,929,085 B2 * | 1/2015 | Franklin et al. | 361/749 |
| 2006/0050475 A1 * | 3/2006 | Chen | 361/683 |
| 2012/0088557 A1 | 4/2012 | Liang | |
| 2012/0212896 A1 | 8/2012 | Schulz | |
| 2012/0235635 A1 | 9/2012 | Sato | |
| 2012/0241247 A1 | 9/2012 | Choe | |
| 2012/0247989 A1 | 10/2012 | Cooper | |

(Continued)

*Primary Examiner* — Forrest M Phillips
(74) *Attorney, Agent, or Firm* — Roark IP

(57) ABSTRACT

A personal cloud structure for a portable computing device such as a tablet personal computer (PC), mobile phones, portable media players, or the like. The personal cloud structure may be fitted with memory, a network connection, two-way wireless charging, external memory slots, external connections and other components to create a portable personal cloud.

22 Claims, 14 Drawing Sheets

(56) References Cited

U.S. PATENT DOCUMENTS

| | | |
|---|---|---|
| 2012/0262345 A1 | 10/2012 | Byun et al. |
| 2012/0268891 A1 | 10/2012 | Cencioni |
| 2012/0270600 A1 | 10/2012 | Zelson |
| 2012/0281356 A1 | 11/2012 | Brewer et al. |
| 2013/0063873 A1 | 3/2013 | Wodrich et al. |
| 2013/0076614 A1 | 3/2013 | Ive et al. |
| 2014/0159867 A1 | 6/2014 | Sartee et al. |
| 2014/0334098 A1* | 11/2014 | Lauder et al. ............ 361/679.56 |

* cited by examiner

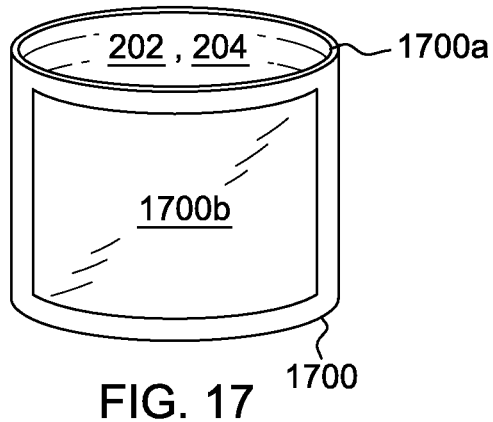
FIG. 17
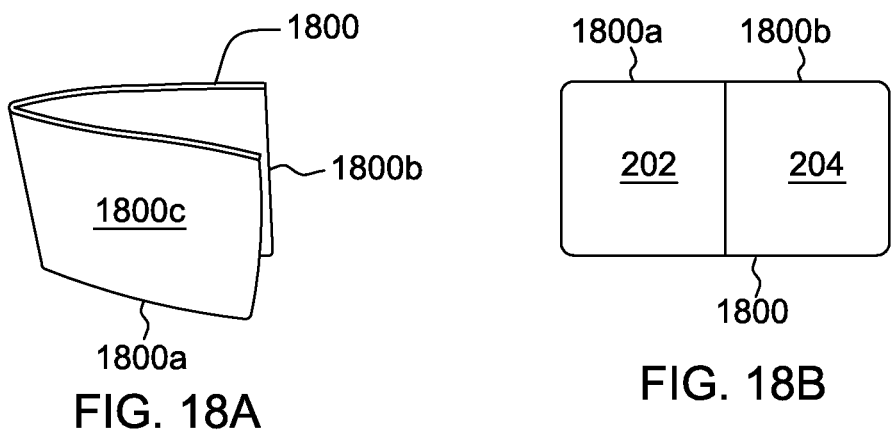
FIG. 18A
FIG. 18B
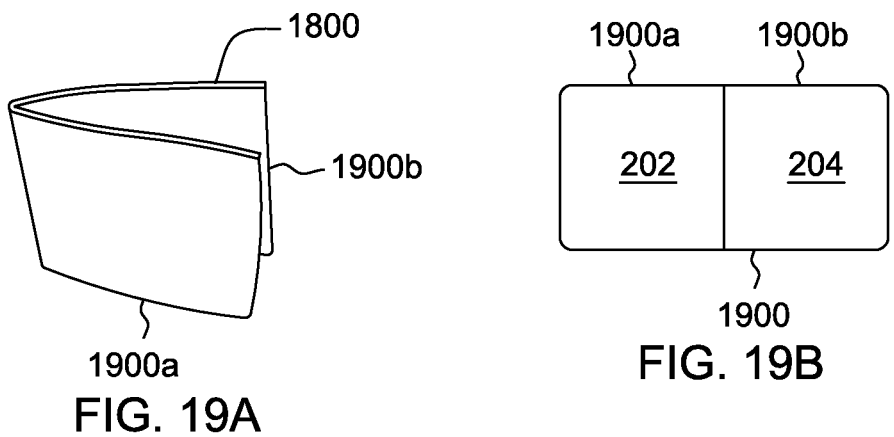
FIG. 19A
FIG. 19B

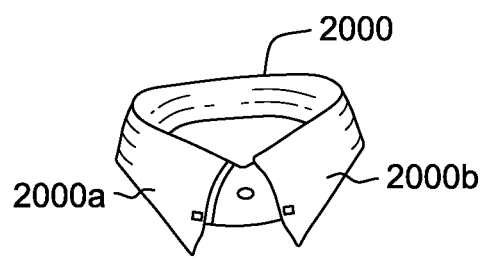
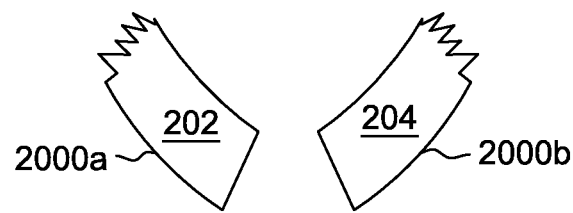
FIG. 20A                FIG. 20B
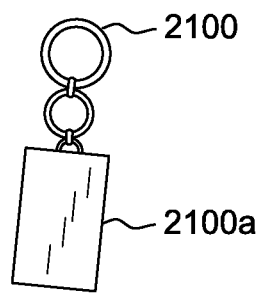
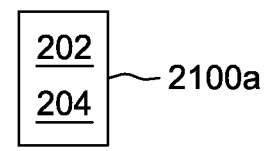
FIG. 21A                FIG. 21B
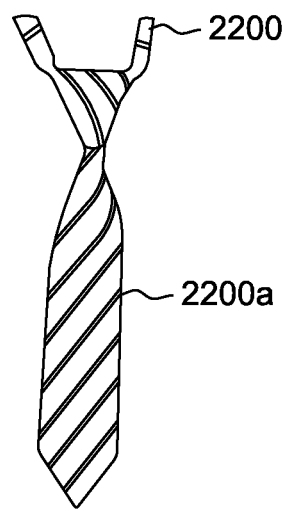
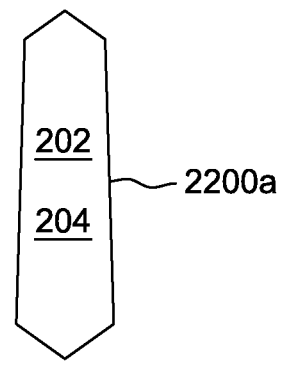
FIG. 22A                FIG. 22B

PERSONAL CLOUD WITH A PLURALITY OF MODULAR CAPABILITIES

PRIORITY CLAIM

This patent application claims the benefit of the U.S. provisional patent application having Ser. No. 61/705,383, filed Sep. 25, 2012; and U.S. application Ser. No. 13/831,663, filed Mar. 15, 2013; the aforementioned applications being incorporated herein by reference in their entirety.

FIELD OF THE DISCLOSURE

The present disclosure relates generally to a system and method of mobile computing and, in particular, in one or more embodiments, the present disclosure relates to structures having a plurality of modular capabilities.

BACKGROUND

There are presently a wide variety of portable electronic devices 102 as disclosed in FIG. 1A. The portable electronic devices may include cellphones such as the iPhone®, Nexus, Lumia and the like and tablet personal computers (PCs) such as the iPad®, Kindle® and similar type devices. These portable electronic devices are often protected by a simple case cover 104 as disclosed in FIG. 1B. These prior art case covers 104 typically do not contain any functional components beyond the protective cover itself.

SUMMARY

Aspects of the embodiments disclosed herein include a structure configured to connect to a mobile computing device comprising: a cavity capable of holding the mobile computing device; a power source coupled to the cavity and to a plurality of modules located in the structure and capable of providing power to the plurality of modules; and wherein the plurality of modules include at least one of a plurality of wireless modems which allows the case to wirelessly transmit and receive signals from other electronic devices.

Other aspects of the embodiments disclosed herein is a case for a mobile communication device comprising: a first panel and a second panel capable of forming a compartment for the mobile computing device; said first panel having a screen; a power source connected to a plurality of modules located on at least one of the first and second panels and capable of providing power to the plurality of modules; and wherein the plurality of modules include a WWAN modem and a WLAN modem which allows the case to wirelessly transmit and receive signals from other electronic devices.

BRIEF DESCRIPTION OF THE DRAWINGS

FIG. 15 shows detachably mounted on a structure a mobile wireless computing device which functions like (and may actually be) an iPad®, iPhone®, PC tablet, Android® based tablet, TouchPad, Nexus 7®, Slate® or the like.

FIG. 17 illustrates an embodiment of the PCCC which has a screen mounted on a band such as a bracelet or sweatband.

FIGS. 18A and 18B illustrate an embodiment of the PCCC which have a screen mounted on a wallet.

FIGS. 19A and 19B illustrate an embodiment of the PCCC which have a wallet shape.

FIGS. 20A and 20B illustrate an embodiment of the PCCC which has a collar shape.

FIGS. 21A and 21B illustrate an embodiment of the PCCC which has a key chain shape.

FIGS. 22A and 22b illustrate an embodiment of the PCCC which has a tie shape.

DETAILED DESCRIPTION

Although particular aspects or features of the following disclosure may be described with reference to one or more particular embodiments and/or drawings, it should be understood that such features are not limited to usage in the one or more particular embodiments or drawings with reference to which they are described, unless expressly specified otherwise. The functionality and/or the features of the embodiments that are described may be alternatively embodied by one or more other devices which are described but are not explicitly described as having such functionality/features.

Current mobile computing device covers are limited in their functionality by mainly providing protection from environmental shocks for mobile computing devices. However, the personal cloud cover case (or "PCCC") as disclosed in this application by providing electronic component accessories and functionalities to the cover case enhances the ability of a mobile computing device located inside the PCCC to provide cloud computing services. (Note: the acronym PCCC may be used herein with regard to the descriptions of FIGS. 14 through 23 to cover similar devices to the personal cloud cover case but not just in the shape of a case cover but rather a wallet, band, collar, key chain, tie, etc.). Cloud computing is the use of computing resources that are delivered as a service over a network (such as the Internet) and which reside in the "cloud". The mobile computing device in the case could be an iPad®, iPhone®, PC tablet, Android® based tablet, Touch-Pad, Nexus 7®, Slate® or the like.

Figure 1B:
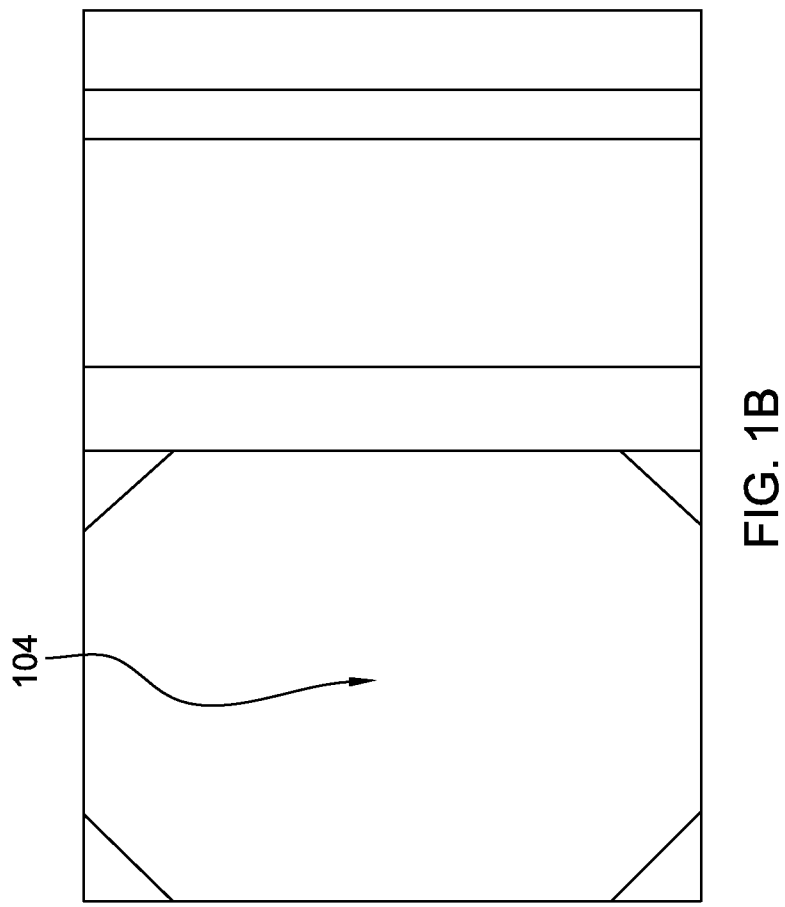
FIG. 1B is a front view of a prior art simple case cover for a mobile computing device.
Figure 1A:
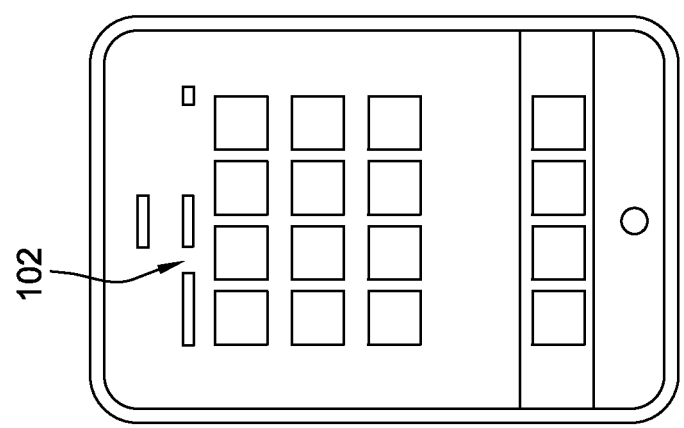
FIG. 1A is a front view of a prior art mobile computing device.
Figure 2A:
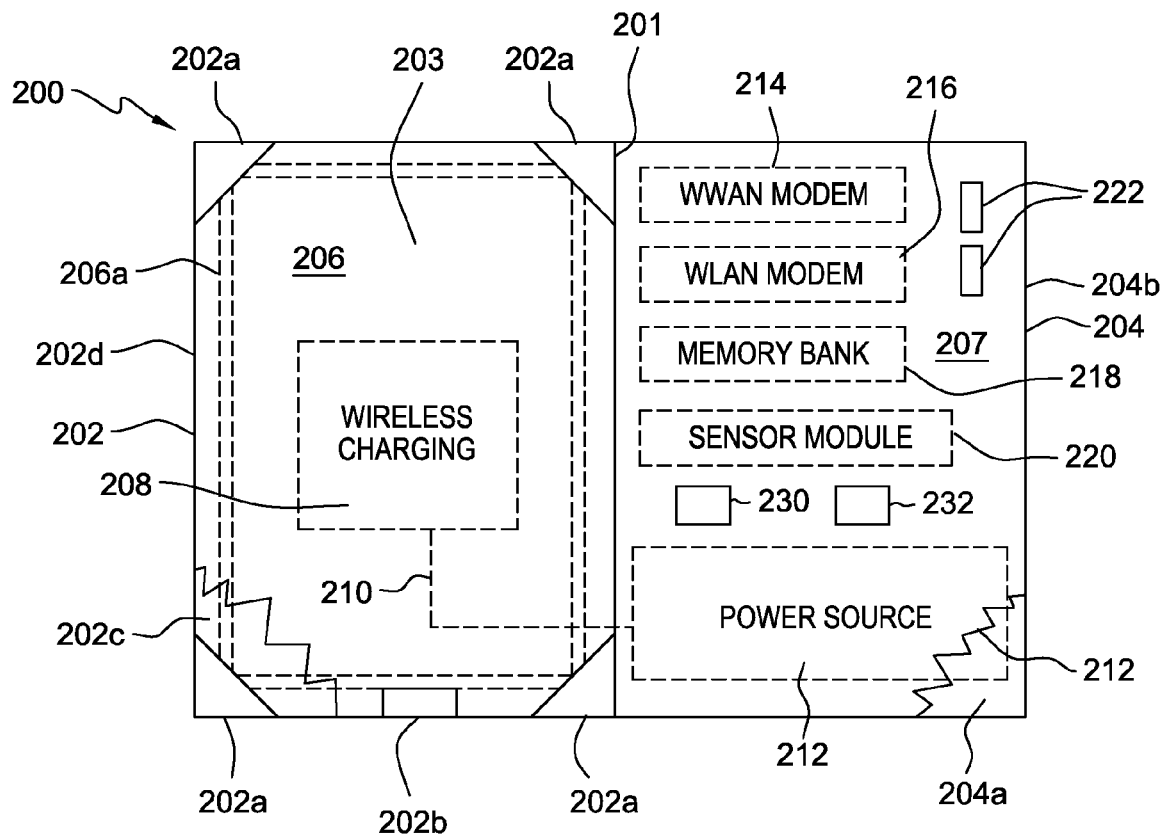
FIG. 2A is a front view of a personal cloud case cover (PCCC).

FIG. 2A is a front view of a PCCC 200 which is shown in an open position. The case 200 provides a personal cloud to the user and access to a wireless network (such as 3G, 4G, WiFi, SuperWifi, and similar technologies) of a mobile computing device (not shown) stored in the case 200. The case 200 may be made of any material (hard and/or soft) that makes the case lightweight but durable and resilient such as plastic, silicone, ceramic, fabric, leather, steel, aluminum, fiberglass, titanium, Kevlar, or rubber. The case 200 could be a continuous piece of material with a flexible (or bendable) area 201 located between two opposing panels (first panel 202 and second panel 204) which pivot together around a compartment 203 for containing the mobile computing device. In an alternative embodiment, the case 200 could be made up of plurality of attached sections (201, 202 and 204). First panel 202 also has 4 sleeves 202a to hold the mobile computing device in place in the case 200. In alternative embodiments, the mobile computing device could be attached to the PCCC 200 using a plurality of magnets (instead of the sleeves 202a) positioned under the mobile device, rubber straps or other similar attachment methods.

The first panel 202 is constructed in layers and includes inner first panel layer 202c, outer first panel layer 202d and embedded circuit board 206. Typically, from the front view the circuit board 206 cannot be seen since it is located underneath the first panel layer 202c shown in cutaway but which is designed to cover substantially the entire first panel 202. An antenna 206a is located on the circuit board 206 and may be in contact with the mobile communication device wirelessly, through physical contact or by connector 202b. Connector 202b is optional and in alternative embodiments it would not be present. The antenna 206a will allow for better transmission and reception on the part of the mobile communication device. The antenna 206a can be a "chip" antenna, printed circuit board (PCB) antenna or the like covering a plurality of wireless bands (e.g., 400 MHz-3.6 GHz). Alternatively, a PCB antenna may be used, and the antenna 206a will be printed directly onto the circuit board 206. Also located on the board 206 is a two-way wireless charging unit 208 which is in substantial proximity to the resting place of the mobile communication device in the cover 200. The charging unit 208 may be designed such that when the mobile communication device is in proximity to the charging unit an electromagnetic field generated by the charging unit pulls the communication device into proper position and alignment for optimal charging (i.e., charging coil alignment). The wireless charging unit 208 is connected through a bidirectional electrical link 210 to power source 212 located on a circuit board 207 embedded in the second panel 204. The bidirectional electrical link 210 is an example of the plurality of electrical connections that are made throughout the case 200 but which are not necessarily shown in the Figures. Link 210 might be in the form of a ribbon cable so as not to be damaged with the opening and closing of the case 200. The wireless charging unit 208 is capable of wirelessly charging the mobile communication device with power received from the power source 212 or wirelessly receive power from the mobile communication device and transfer it to the power source 212. The wireless charging unit 208 may operate by magnetic resonance, inductive charging, or power over radio frequency (RF) or similar wireless charging methods. The power source 212 is used to power the plurality of components located throughout the cover 200 and, as described, can also be used as a backup battery for the mobile computing device when the voltage in the battery of the mobile computing device falls below a predetermined level.

The second panel 204 can be made up of an inner second panel 204a and an outer second panel 204b containing the embedded circuit board 207 but which typically cannot be seen from a front view since it is covered by inner second panel layer 204a. The inner second panel layer 204a covers substantially the entire second panel 204 but is only partially shown in cutaway so as to illustrate the components mounted on the circuit board 207 in the outer second panel 204b. It should be understood that the inner second panel layer 204a and the outer second panel layer 204b can be coupled together by a variety of methods such as ultrasonic bonding, mechanical fasteners, adhesives, or solvents. In alternative embodiments, the inner second panel 204a may be entirely or substantially detachable from the outer second panel 204b; the inner second panel 204a may be a closure flap that is fastened close by means of adhesive, a snap button, or Velcro or the inner second panel 204a may not be present at all so as to allow easy access to the components mounted on the board 207 in the outer second panel 204b. The case 200 may further be made up of a plurality of modules 214, 216, 218 and 220 mounted on the circuit board 207 which allow the PCCC 200 to have multi-functional capability. The modules may be made of low profile components which help minimize the thickness of the cover. The plurality of modules may be permanently mounted, may snap-in to the board 207 or may be some combination thereof. First module 214 may include a wireless wide area network modem (WWAN). The WWAN could include baseband, a radio frequency integrated circuit (RFIC), a radio frequency front-end module (RF FEM), Envelope Tracking (ET), Power Management IC (PMIC), and other connected components to link the mobile computing device to a mobile network such as a 3G, 4G or future generation network. Second module 216 may include a wireless local area network (WLAN) modem for a mobile computing device to connect to a local router and then to 2G, 3G and 4G networks. The WLAN modem can be baseband, RFIC, RF FEM and other connectivity components. The case 200 may contain near field communications (NFC) technology which may be used for contactless shortrange communications based on RF identification standards (RFID) using magnetic field induction to enable communication between the electronic components in the case 200 over short distances such as a few centimeters. In other embodiments, the WLAN modem connection could be made using wireless protocols such as WiFi, SuperWiFi (i.e., the next generation WiFi with superior range), Bluetooth, wireless for high definition multimedia interface (WHDMI), or the like. Third module 218 may be internal storage such as solid-state drives (SSD) or flash memory (e.g., MultiMedia Card (MMC), electronic MMC (eMMC) or the like). Fourth module 220 may contain a sensor chip that is able to detect biometrics inputs such as finger prints, eye movement, face shape, and the like. Module 220 can be used for functions such as a security feature for allowing or denying access to the electronic components in the case, gaming, and medical purposes (e.g., measuring blood cell count and the like). The second panel 204 may also include a smart feature such as a synchronization input 230 (e.g., such as a button, touch screen, or the like) that allows the plurality of electronic components (e.g., module 218) in the PCCC 200 to be synched to other networked devices in the cloud when operated. This input 230 would primarily be used when a mobile communication device is not present in the PCCC 200. The input 230 may be used to backup data stored in the components of the PCCC 200. Reference 232 in FIG. 2A shows a controller which may be used with the mobile communication device or in the absence of the mobile device to control the electronic components in the PCCC 200. For example, in the synching process when input 230 is operated the controller 232 would direct the synching operation.

Figure 2B:
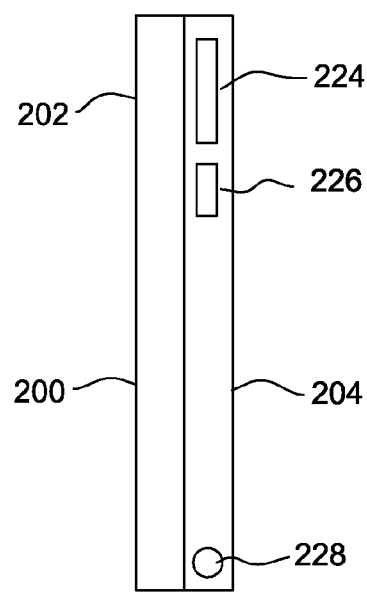
FIG. 2B is a side view of the PCCC of FIG. 2A.

FIG. 2B is a side view of the case 200 in a closed position. Data connection ports 224 and 226 provide communication capabilities to the case 200. Ports 224 and 226 may be a mini universal serial bus (USB), micro universal USB port or an audio visual (A/V) connector such as a high definition multimedia interface (HDMI) port and the like. Charging port 228 can be connected to the grid or other power source to feed the power source 212.

Figure 3:
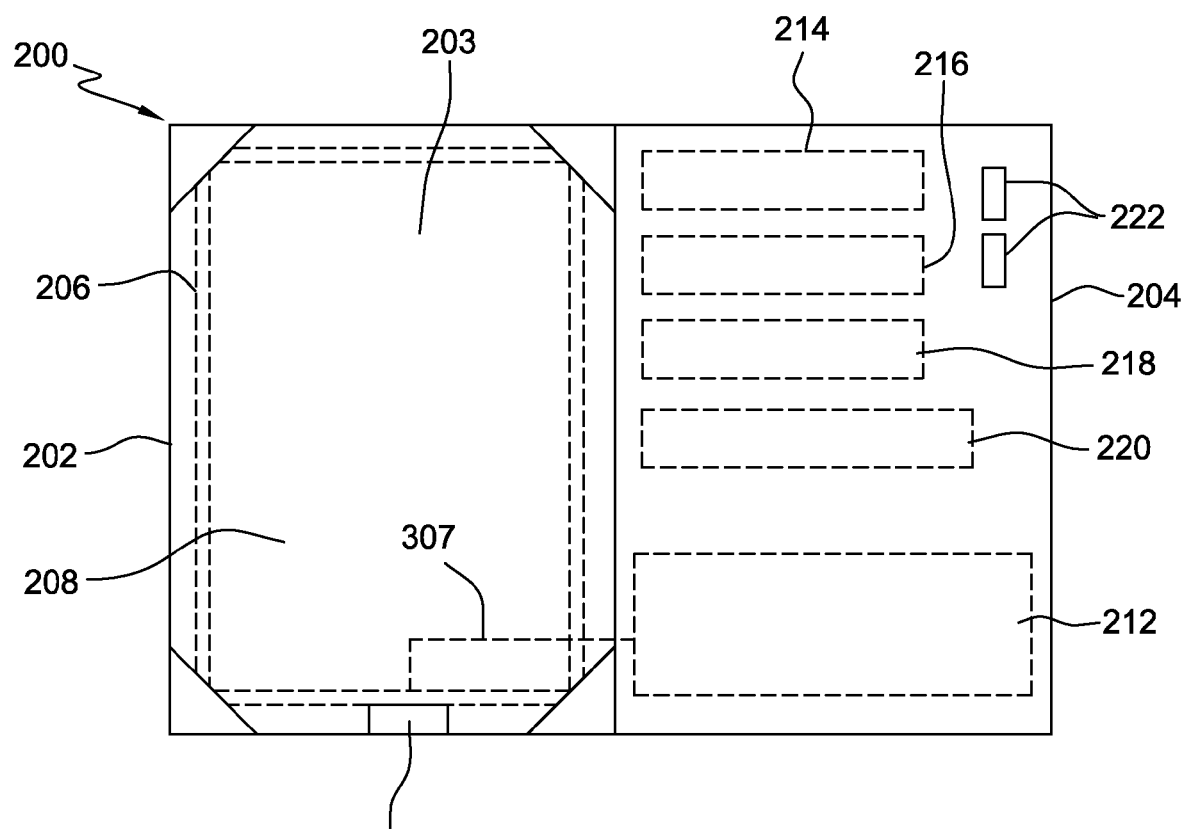
FIG. 3 is a front view of a second embodiment of the PCCC.

FIG. 3 is a second embodiment of the PCCC 200. Common numbering is used in FIGS. 3 through 9 and FIGS. 2A to 2B to denote similar elements. In this second embodiment, instead of wireless charging, a docking bay 305 having a set of electrical contacts is configured to electrically engage with the input/output contacts on a mobile communication device. The docking bay 305 may be a standard connector that allows the mobile communication device to receive power through line 307 from power source 217.

Figure 4:
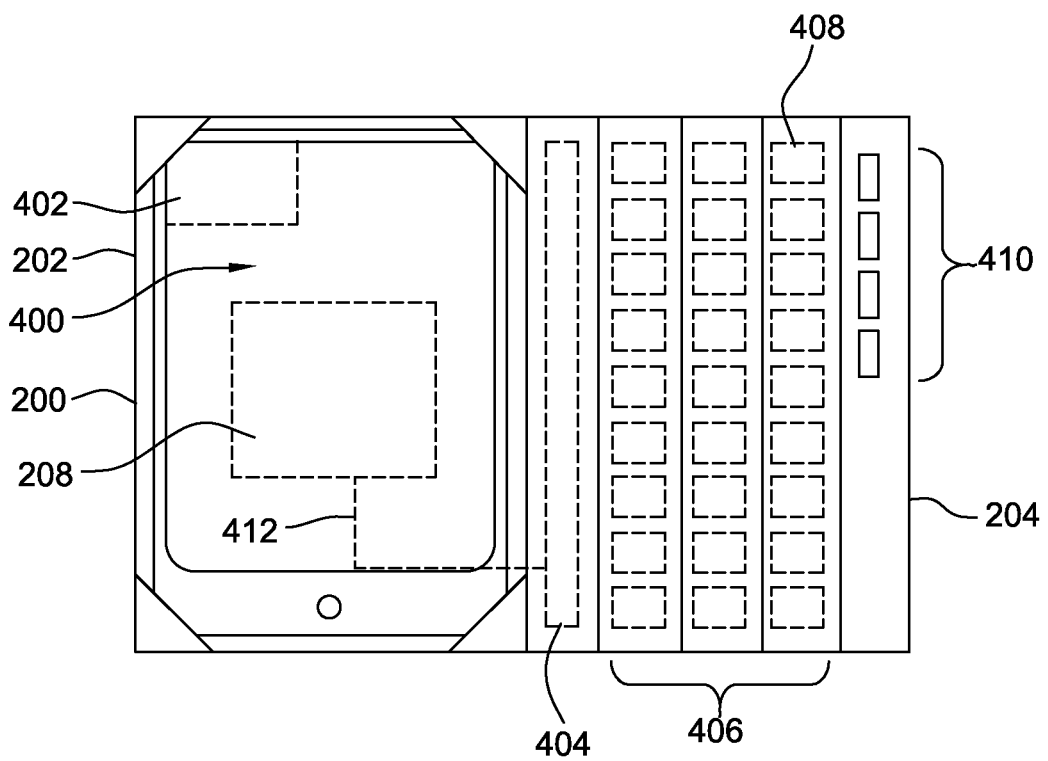
FIG. 4 is a front view of a third embodiment of the PCCC.

FIG. 4 illustrates a third embodiment of the PCCC 200. A mobile communication device 400 can be connected to a local area or wide area network through wireless modem 402 which may be 3G, 4G, 3G/4G, WHDMI, Bluetooth, WiFi, SuperWiFi, and other wireless standard. Module 404 is a replaceable, rechargeable battery that is charged through line 412 from the wireless charger 208 and receives power from mobile communication device 400. Module 404 performs the same function as power source 212 in FIG. 2 but is arranged differently in the case 200 as shown in FIG. 4. The wireless charger 208 may be located on the first panel 202 beneath the mobile communications device 400. The module 404 can also be charged from a power outlet when the case 200 is plugged in. The module 404 can be used as a power source for other modules (reference numerals 408 and 410 as discussed below) located in the case 200. An embedded memory bank 406 includes a plurality of memory modules and is mounted on the second panel 204. The memory bank modules may be 500 MegaByte (MB), 1 Gigabyte (GB), 1 Terrabyte (TB) or the like in memory size. Memory slots 410 are capable of holding additional memory such as removable micro-Secure Digital (micro-SD) memory cards for storage expansion.

Figure 5:
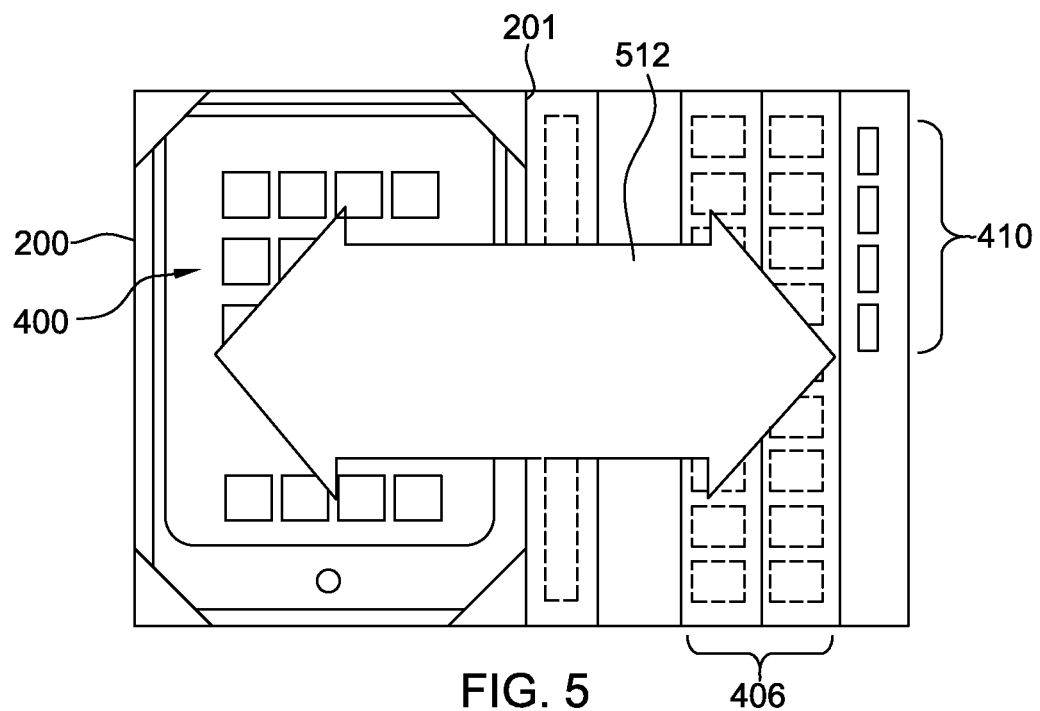
FIG. 5 is a front view of a fourth embodiment of the PCCC.

FIG. 5 illustrates a fourth embodiment of the PCCC 200 which demonstrates that the plurality of modules are detachable and could be two instead of three in the case 200. Also, FIG. 5 discloses a wireless data connection 512 between the device 400 and memory bank 406 using WiFi, SuperWiFi or Bluetooth protocols. In alternate embodiments, the data connection 512 could be a hardwired such as a Universal Serial Bus (USB), microUSB, miniUSB, or HDMI (with the data line being flexibly bendable across the flexible region 201 in the form of a ribbon cable or the like). In other embodiments, the connection could also be an optical wireless link or cable such as infrared. The data transfer could be bi-directional to allow for read and write both ways from device 400 to memory 406 and from memory 406 to device 400.

Figure 6A:
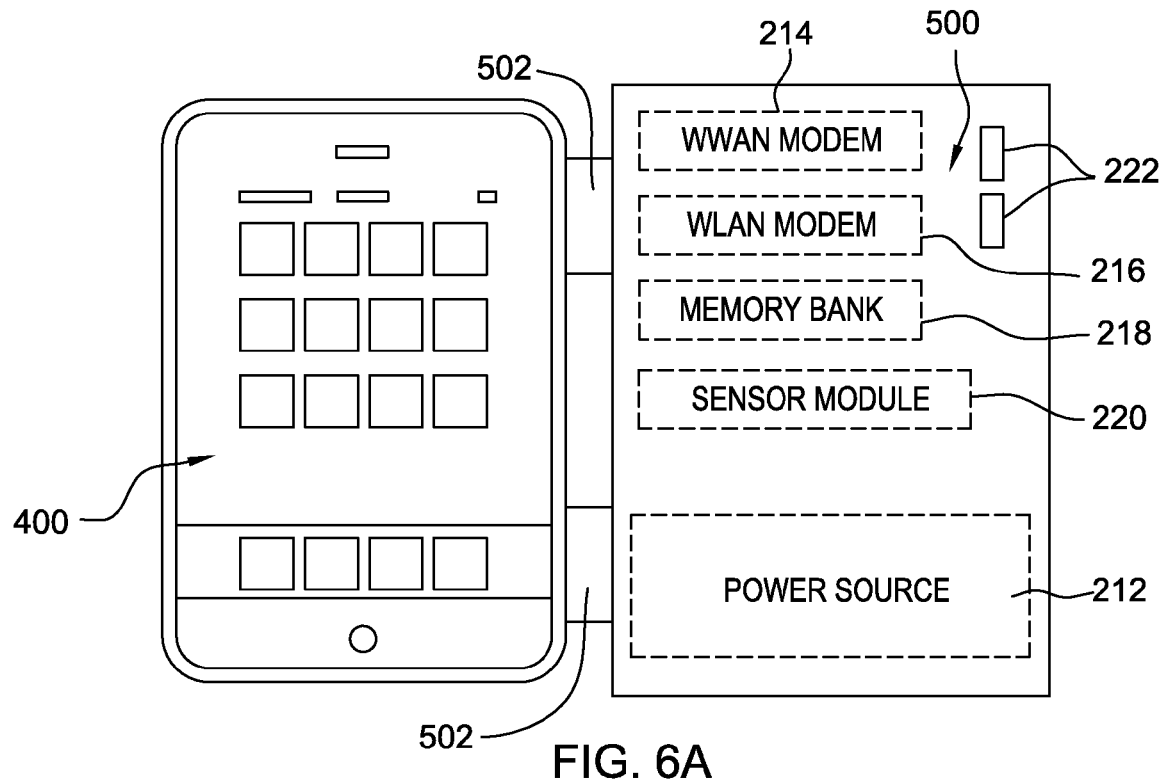
FIG. 6A is a front view of a fifth embodiment of the PCCC.
Figure 6B:
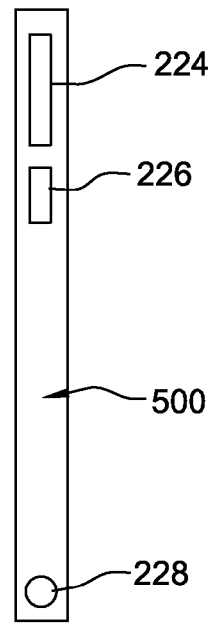
FIG. 6B is a side view of the PCCC of FIG. 6A.

FIG. 6A is another embodiment of the PCCC with just one panel 500 attached to the device 400 through attachments 502. Attachments 502 may be magnets, clip ins, connectors or some other type of hinge. The attachments 502 may internally include a plurality of electrical links to provide power from the power source 212 to the mobile communication device 400 as well as provide data communications between the modules on the panel 500 and the device 400. The power source 212 may include a wireless charging unit so as to wirelessly charge the device 400. The charging may take place when the panel 500 is in a lateral position relative to the device 400 as shown in FIG. 6A. In an alternative embodiment, the panel 500 may be folded over and placed in contact with the device 500 to establish an electrical power link between the power source 212 and electrical contacts located on the device 400. Also, similar to the embodiment of FIG. 5, a wireless data connection may be established between the device 400 and the plurality of modules on the panel 500 (items 214, 216, 218, 220, and 222). FIG. 6B is a side view of the panel 500 showing the connection ports 224, 226, and 228 which serve the same functions as described in connection with FIG. 2B above.

Figure 7:
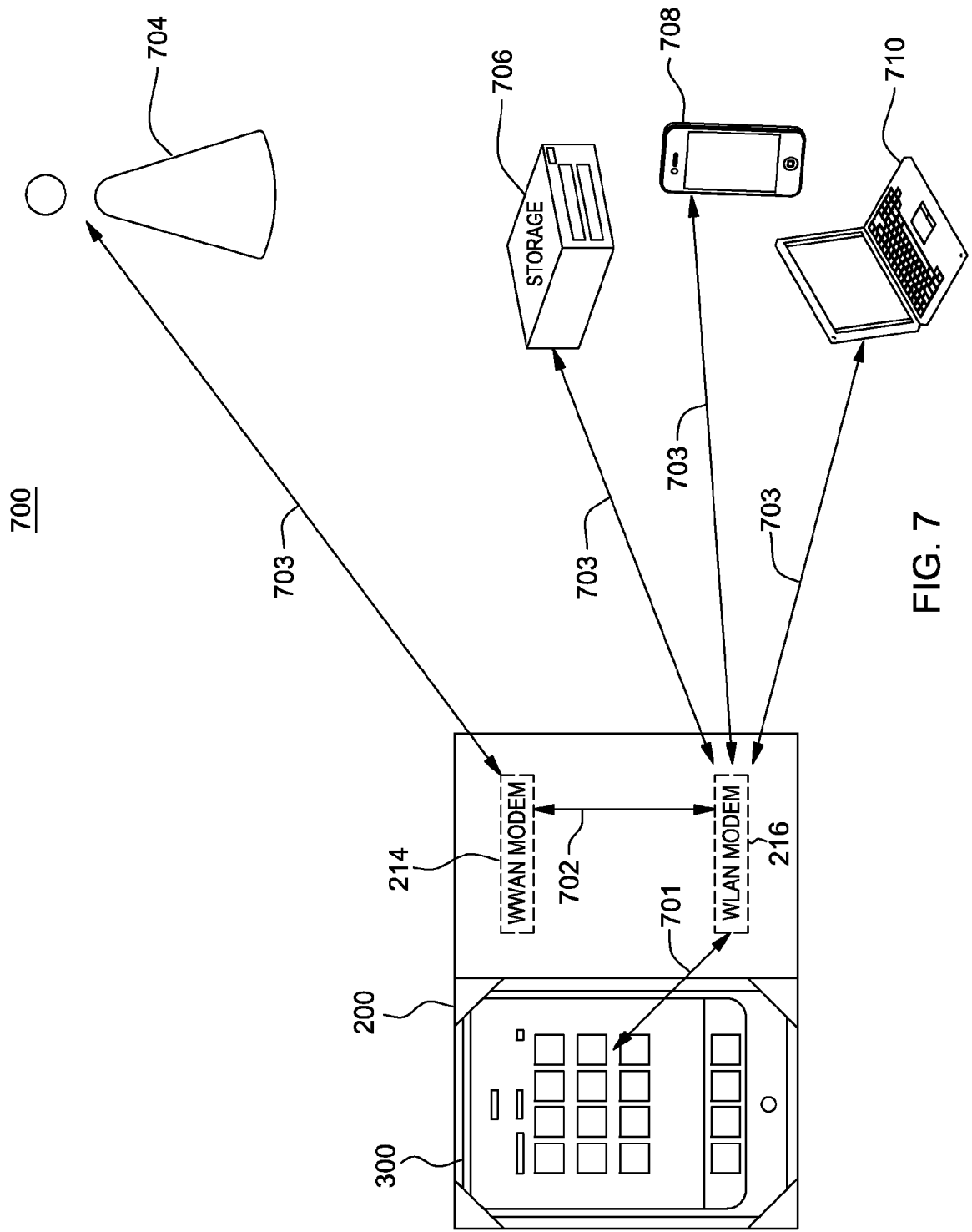
FIG. 7 is a schematic diagram of a PCCC in a cloud/networked environment utilizing 3G, 4G and similar wireless connections.

FIG. 7 illustrates the mobile communication device 300 and PCCC 200 operating in a cloud (or networked) environment 700. Storage 706, mobile phone 708 and personal computer (PC) 710 are part of the cloud upon which the mobile communications device 300 and PCCC 200 can exchange data and synchronize through a plurality of wireless links 703. The WWAN modem module 214 and the WLAN modem module 216 of FIG. 7 operate in a similar manner as described in connection with FIG. 2A above. The mobile computing device 300 communicates through a bi-directional wireless link 701 with the WLAN modem 216 using Bluetooth, WiFi, SuperWiFi and similar wireless standards. In another embodiment, the link 701 may be a wired link. WLAN modem 216 then can read and write wirelessly in a local environment with storage 706. The WLAN modem 216 can also communicate with another mobile phone 708 and PC 710. Alternatively, the mobile computing device 300 can communicate through WLAN 216 over a bi-directional link 702 with WWAN modem 214. WWAN modem 214 can communicate wirelessly using 3G/4G protocols over longer distances than the WLAN modem 216 with a cell tower 704 and then to the Internet. In the environment of FIG. 7, the case 200 is acting as "hotspot". As a hotspot, the case 200 offers network (e.g., Internet) access over the WWAN modem 214 or WLAN modem 216.

Figure 8:
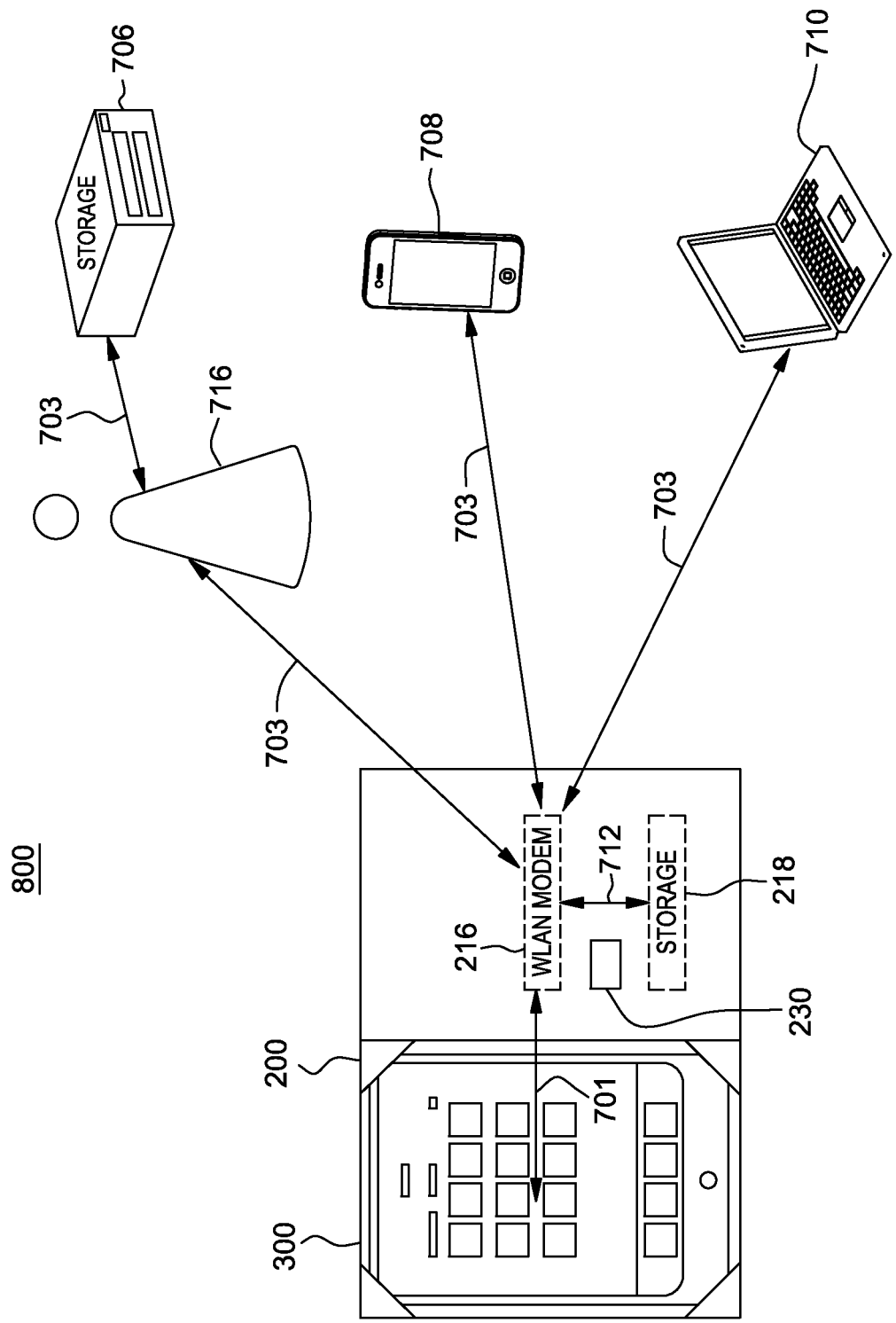
FIG. 8 is a schematic diagram of the PCCC in another cloud/networked environment system.

FIG. 8 illustrates another variation of the mobile communication device 300 and the case 200 in operation 800. This arrangement allows the local storage 218 to have access to a plurality of devices in the cloud such as the communication device 708, PC 710 and storage 706 through local wireless router (or access point) 716. As previously discussed in connection with FIG. 2A, sync input 230 can be operated when the mobile communication device is not present in the case 200 to backup all data contained in the components in the case 200 to the cloud (e.g., devices such as 706, 708, 710 and other devices). Another advantage is that this system allows for the formation of a "pass through Internet" from the mobile communication device 300 to devices 706, 708, 710 and a network (e.g., the Internet). WLAN modem 216 is connected to memory storage 218 through link 712 and is capable of establishing wireless communications with both the mobile communication device 300 and the devices 706, 708, and 710. In operation, the mobile communication device 300 establishes a wireless connection 701 through WiFi, SuperWiFi, 4G or the like to the WLAN modem 216. Through WLAN modem 216, the communication device 300 is capable of connecting to the memory storage 218 (e.g., providing information or instructions regarding reading and/or writing) while simultaneously browsing the Internet through wireless link 703 to access point 716. The term simultaneously as used herein shall mean immediate or nearly immediate succession in time. In another embodiment, the connection from the mobile communication device to the memory storage 218 could be wired. Alternatively, the communication device could be simultaneously connecting to memory storage 218 while communicating with devices 706, 708 and 710 through wireless links 703. This pass through Internet feature allows the user to access data stored in the memory 218 and browse the Internet simultaneously from a single device (mobile communication device 300) or a plurality of devices. The WLAN modem 216 is designed to operate in one or more bands and cover one or more wireless standards. The bands may include first and second frequency bands (e.g., 2 GHz and 5 GHz). The WLAN modem 216 may use the first band for the transmission of information from memory storage 218 to the mobile communication device 300 and the second band for communications with the access point 716 (and thereby the Internet).

Figure 9:
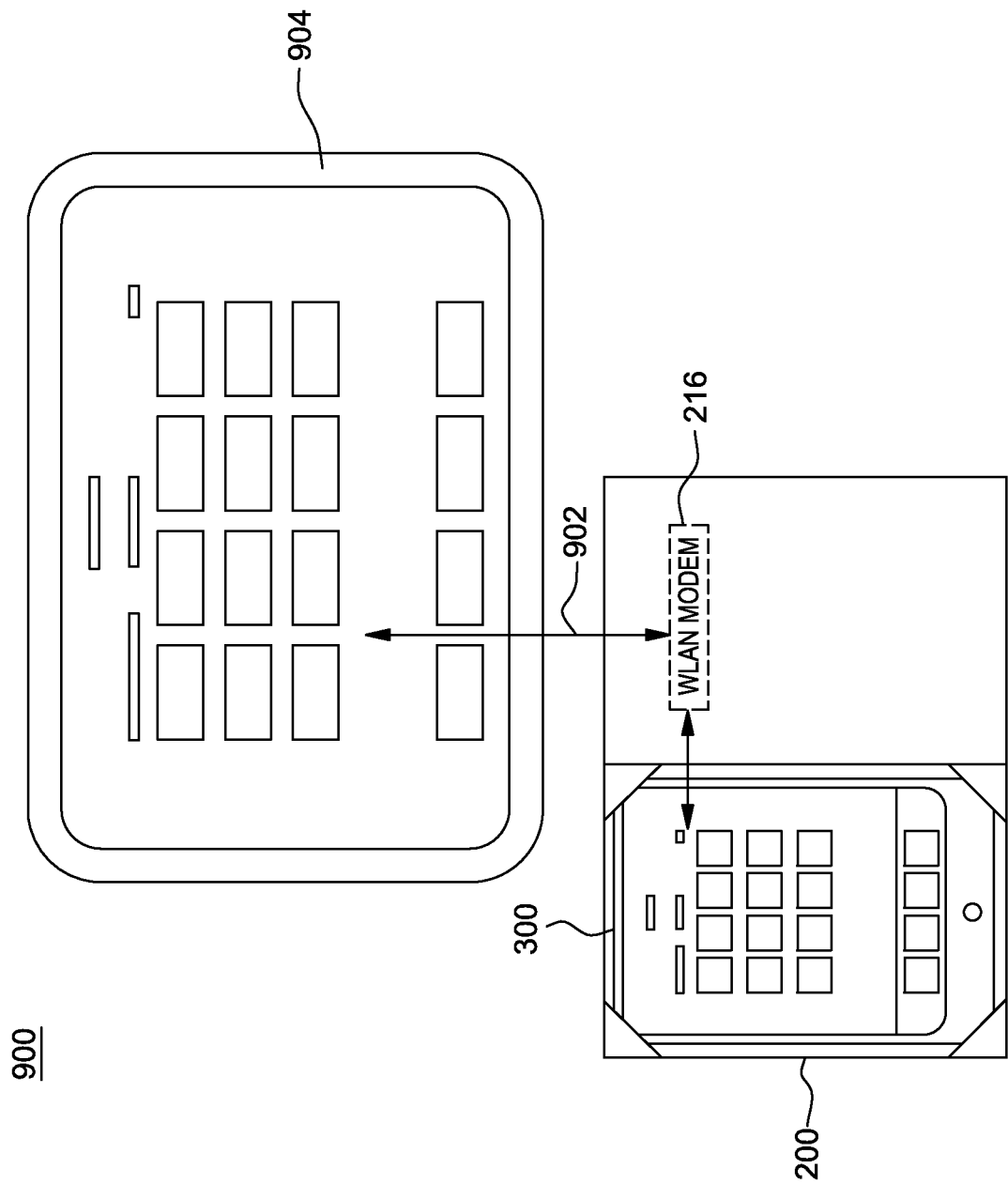
FIG. 9 is a view of the PCCC operating with a large external monitor.

FIG. 9 illustrates another environment 900 in which the PCCC 200 may operate. The PCCC 200 allows the mobile communication device 300 to link through WLAN 216 and wireless link 902 with large external monitor 904 using WiFi, SuperWiFi, WHDMI, or the like and display information (e.g., video, audio, or text) from either the mobile communication device 300, the memory storage or another source (e.g., devices 706, 708, 710) on to the monitor 904.

Figure 10:
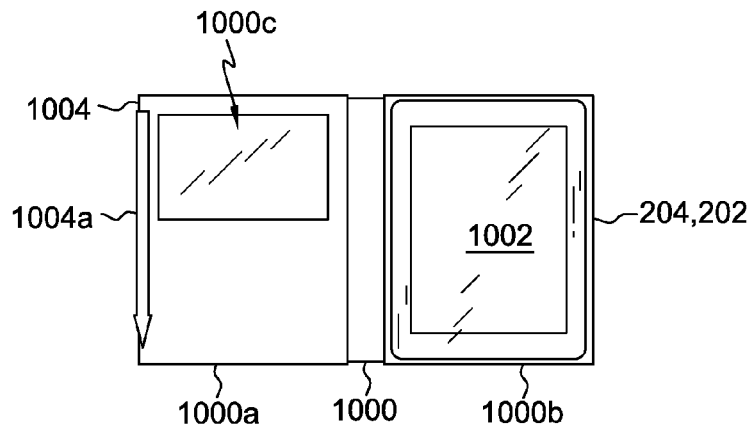
FIG. 10 is a front view of another embodiment 1000 of the PCCC which has a window in the left panel.

FIG. 10 is a front view of another embodiment 1000 of the PCCC which is shown in an open position. As previously discussed, the mobile computing device 1002 in the case 1000 could be an iPad®, iPhone®, PC tablet, Android® based tablet, TouchPad, Nexus 7®, Slate® or the like. Embodiment 1000 and embodiments 1100, 1200, 1300, 1400, 1700, 1800, 1900, 2000, 2100, 2200, and 2300 discussed below operate in a manner similar to the other embodiments of the PCCC disclosed above in the discussions of FIGS. 2A through 9. In embodiment 1000, however, the mobile computing device 1002 is mounted on the right (or second) panel 1000b of the case cover. Embodiment 1000 may provide a personal cloud to the user and access to wireless networks (such as 3G, 4G, WiFi, SuperWiFi, and similar wireless technologies). The right panel 1000b includes the electronic components, modules (including WLAN and WWAN wireless modules), memory and power source as described above with regard to second panel 204 in FIG. 2A. However, it is also includes the wireless charging module 208 which is shown FIG. 2A mounted on the first panel 202. So panel 100b includes the components of both 202 and 204 of FIG. 2A. In this embodiment 1000, the left (or first) panel 1000a of the case cover has a window 1000c which allows for a view of either all or part of the screen of the mobile device 1002 when the case is closed. For example, the window 1000c might be approximately one quarter to approximately one half the surface area of the left panel 1000a. The case 1000 also has an attachment 1004 for a stylus 1004a such as a pressure sensitive pen.

Figure 11:
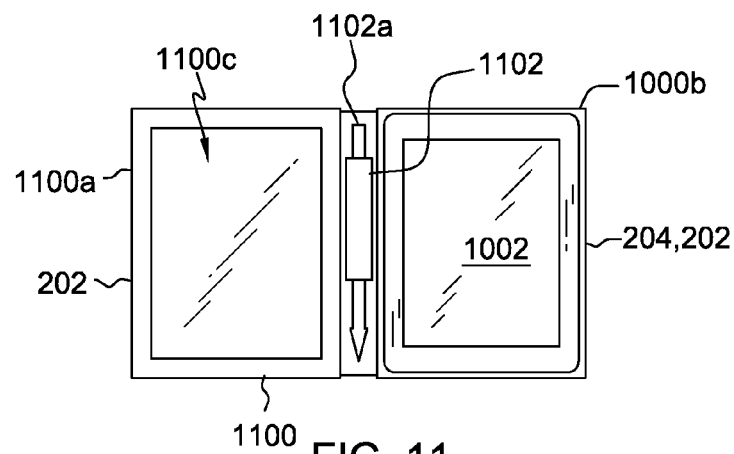
FIG. 11 illustrates an embodiment of the PCCC which has an embedded screen mounted on the left panel cover.

FIG. 11 illustrates an embodiment 1100 of the PCCC which has an embedded (or mounted) screen 1100c on the left (or first) panel cover 1100a. The mobile computing device 1002 is mounted on the right (or second) panel 1100b. Embodiment 1100 may provide a personal cloud to the user and access to wireless networks (such as 3G, 4G, WiFi, SuperWiFi, and similar wireless technologies). The right panel 1100b includes the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. In alternative embodiments, the wireless charging module 208 can be embedded in the left panel 1100a and provide power to the screen 1100c as shown in FIG. 2A mounted on the first panel 202. The screen of the mobile computing device 1002 and the screen 1100c each may be an organic light emitting diode (OLED), light emitting diode (LED), liquid crystal display (LCD), Mirasol®, E Ink or the like. The screen 1100c could have an embedded digitizer for drawing, writing and taking notes and be pen input sensitive. The embodiment 1100 has a holder (or attachment) 1102 for an input pen 1102a.

Figure 12:
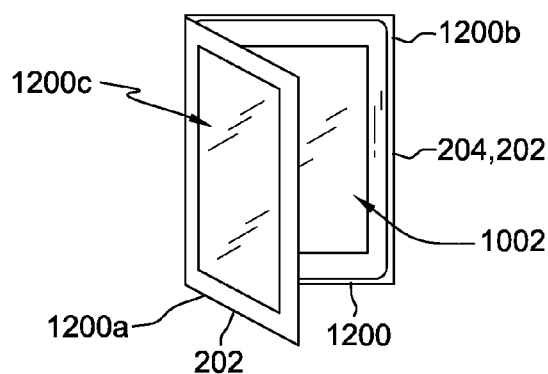
FIG. 12 illustrates an embodiment of the PCCC which has an embedded screen mounted on the outside of the left panel cover with the mobile device mounted in the right panel.
Figure 13:
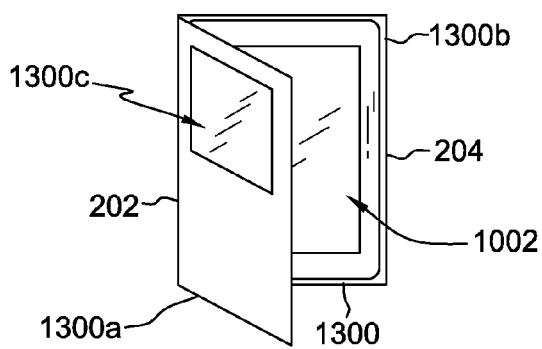
FIG. 13 shows a similar embodiment of the PCCC to that of FIG. 12 with an embedded screen also mounted on the outside of the left panel with the mobile device mounted on the right panel.

FIG. 12 illustrates an embodiment 1200 of the PCCC which has a screen 1200c (which may be embedded) mounted on the outside of the left panel cover 1200a with the mobile device 1002 located in the right panel 1200b. FIG. 13 shows a similar embodiment 1300 of the PCCC with an embedded screen 1300c also mounted on the outside of the left panel 1300a with the mobile device 1002 mounted on the right panel 1300b. However in this embodiment, the screen 1300c covers approximately twenty-five percent to approximately half the surface of the left panel 1300a. The right panels 1200b and 1300b includes the electronic components, modules (including WLAN and WWAN wireless modules), memory and power source as described above with regard to second panel 204 in FIG. 2A. However, the panels 1200b and 1300b may also include the wireless charging module 208 which is shown in FIG. 2A mounted on the first panel 202. In an alternative embodiment, the wireless charging module 208 can be embedded in the left panels 1200a and 1300a and provide power to the screens 1200c and 1300c as shown in FIG. 2A with regard to first panel 202. The screen of the mobile computing device 1002 and the screens 1200c and 1300c each may be an OLED, LED, LCD, Mirasol®, E Ink or the like. The screen 1200c and 1300c could have an embedded digitizer for drawing, writing and taking notes and be pen input sensitive.

Figure 14:
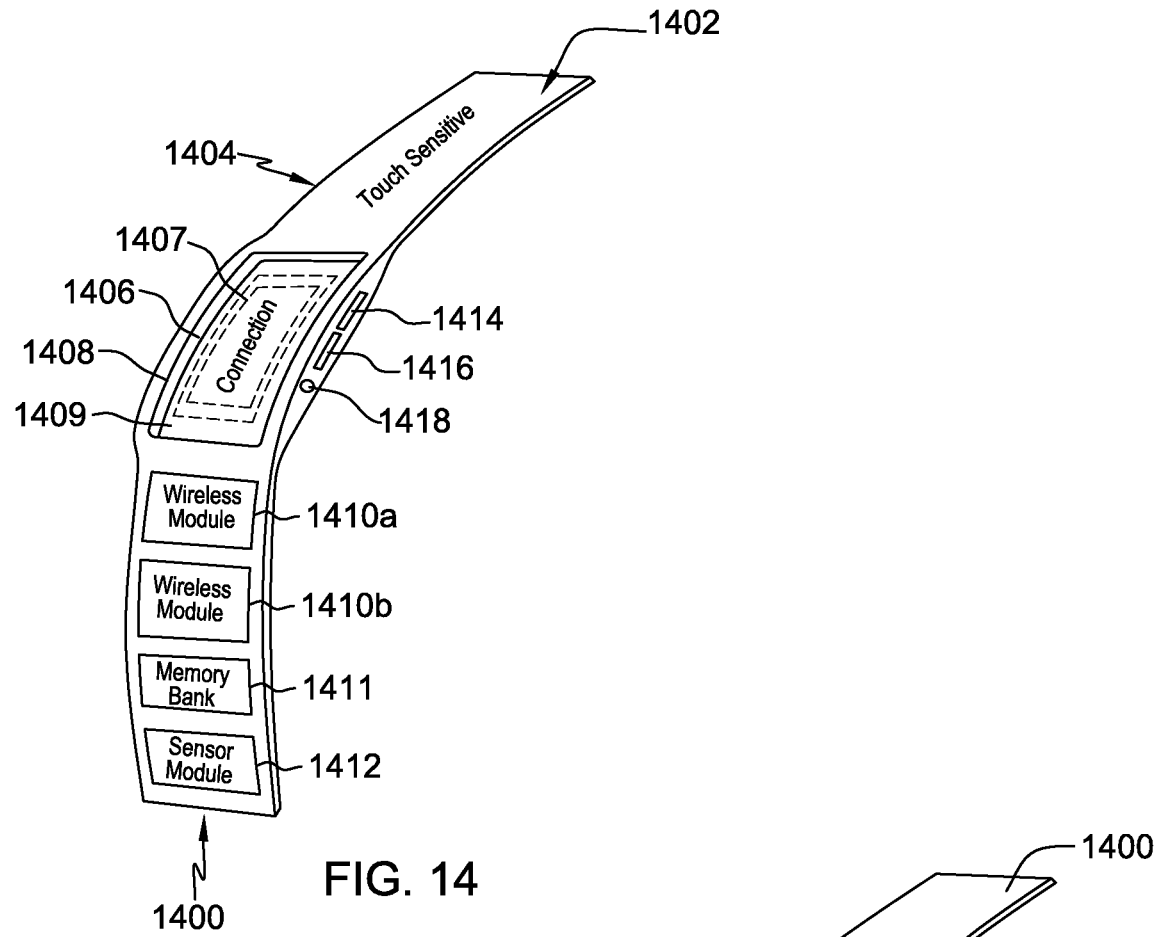
FIG. 14 illustrates an embodiment which operates in a manner similar to the other embodiments of the PCCC disclosed above in the discussions of FIGS. 2A-13 but instead the electronic components are mounted on a structure such as a band instead of a case.

FIG. 14 is a view of another embodiment 1400 of the PCCC. Embodiment 1400 operates in a manner similar to the other embodiments of the PCCC disclosed above in the discussions of FIGS. 2A-13 but instead the electronic components are mounted on a structure such as a band instead of a case. Embodiment 1400 provides a personal cloud to the user and access to wireless networks (such as 3G, 4G, WiFi, SuperWiFi, and similar wireless technologies). The structure 1400 may be a watch-type band made of waterproof material and manufactured by injection molding. Electronics components in the band such as controllers, memory modules, batteries, and the like may be entirely covered by the structural material. In alternative embodiments the structure 1400 may be made of any material (hard and/or soft) that makes the embodiment 1400 lightweight but durable and resilient such as plastic, silicone, ceramic, fabric, leather, steel, aluminum, fiberglass, titanium, Kevlar, and/or rubber. The surface of the structure itself may be touch sensitive 1402 to communicate with a mobile device located on the band in cavity 1406 or nearby. The band may be substantially circular or substantially oblong in shape and be capable of being wrapped around the hand, wrist, forearm, bicep, head, or leg of the wearer or around the wearers' clothing such as a hat (or helmet). The band should have some type of clasping device (e.g, Velcro, metal clasp, etc.) mounted on each of the ends of the band for attachment. A cavity 1406 is located in the band and, typically, in the central portion of the band. Wireless charging circuitry 1404 may be in electrical connection with cavity 1406 and may extend out from both sides of cavity 1406. The wireless charging circuitry can provide both power and serve as a data link. For example, the wireless charging circuitry 1404 may be connected to the touch sensitive surface 1402 to communicate data to the mobile device in the cavity 1406. The wireless charging circuitry 1404 may be ribbon cable so that it flexibly bends with the band. Wireless charging circuitry 1404 may be internal to the band and extend along substantially the length of the band. The wireless charging circuitry 1404 may be connected to electronic modules and components mounted on the band such as modules 1410 and 1412 and memory bank module 1411 (which may be made up of a plurality of memory modules). The wireless charging circuitry 1404 is configured to transfer power from at least one, several or all of the of the modules to a mobile computing device mounted in the cavity 1406 or may transfer power from the mobile computing device in the cavity to at least one, several or all of the modules 1410, 1411, and 1412. Similar to synchronization button 230, the band may also have an input (such as the touch sensitive screen 1404) configured to direct the plurality of electronic components to receive synchronization information from a wireless network.

Cavity 1406 contains antenna 1407 which may be mounted on a miniature wireless charging unit 1408 or mounted separately. Wireless charging unit 1408 is connected to wireless charging circuitry 1404 and may operate by magnetic resonance, inductive charging, or power over RF or similar wireless charging methods to charge an a mobile communication device mounted in the cavity 1406. Along with the wireless charging unit 1408 there may be a battery 1409 located in the cavity and in connection with the wireless charging unit 1408 and the wireless charging circuitry 1404. Reference numerals 1414 and 1416 indicate data ports providing outside connections to cavity 1406. Data ports 1414 and 1416 may be microUSB, HDMI, NV inputs or the like and are linked to both the mobile communication device in the cavity 1406 and over wireless charging circuitry 1404 to the modules 1410a, 1410b, 1411, and 1412. Port 1418 may be a charging port to provide power to the wireless charging unit 1408 and/or battery 1409 located in the cavity 1406 and ultimately to the mobile communication device and the electronic components in the band. Electrically connected to the cavity 1406 is a wireless modules 1410a and 1410b. Wireless module 1410a may be a WWAN modem to link the electronic device to 3G, 4G or other future network. Wireless module 1410b may be a WLAN modem to link the electronic device using WiFi, SuperWiFi, Bluetooth, WHDMI, or the like. Functionally modules 1410a and 1410b operate similarly to modules 214 and 216 as described above. Memory bank 1411 (similar to memory bank 218) may include a plurality of replaceable memory modules having internal storage such as SSD, flash memory, or the like. Since the memory bank 1411 (and its memory modules) are coupled (or in communication) with the wireless modems 1410a and 1410b, the band is therefore configured to allow for simultaneous connection of the mobile communication device with the memory bank 1411 and through the wireless modem to a network. Module 1412 (similar to module 220) may be a sensory module and may contain a sensor chip which can detect biometric inputs such as finger prints, eye movement, face shape and the like.

Figure 15:
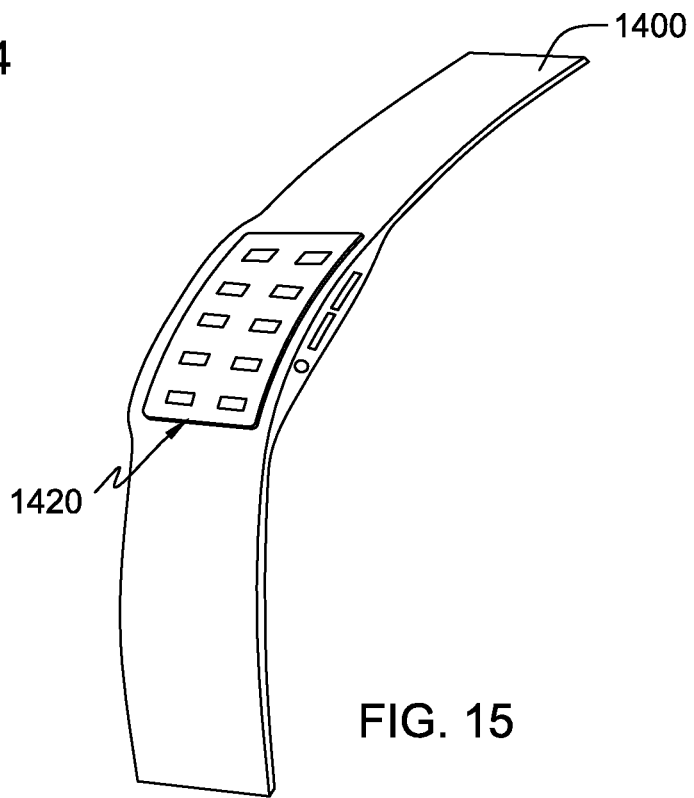

FIG. 15 shows detachably mounted on the structure 1400 a mobile wireless computing device 1420 which functions like (and may actually be) an iPad®, iPhone®, PC tablet, Android® based tablet, TouchPad, Nexus 7®, Slate® or the like. Cavity 1406 may be designed to allow the mobile computing device 1420 to be snapped into position in the cavity 1406. The form factor of the mobile computing device 1420 can be the typical size of these devices and be mounted substantially lengthwise with the band or substantially perpendicular to the direction of the band. The form factor of the computing device 1420 can also be approximately the size of a watch or a watch phone having a rectangular or square shape with outside dimensions such as: length in the range of 22 mm to 44 mm; width in the range of 22 mm to 44 mm; and height (or thickness) in the range of 4 mm to 18 mm. The screen sizes of these computing devices can also be rectangular or square and be in the ranges such as: length 18 mm to 42 mm; width in the range of 18 mm to 42 mm; and height (or thickness) in range of 2 mm to 4 mm. In the case of substantially circular profiles the dimensions may be: diameter in the range of 22 to 44 mm and height (or thickness) in the range of 4 mm to 18 mm with substantially circular screens having dimensions of: 18 mm to 42 mm and height (or thickness) 2 mm to 4 mm. Further, the mobile computing device 1420 can be flexible. The device 1420 can be mounted in or on top of the cavity 1406 using a mechanical attachment (e.g., snap-in) or a magnetic coupling. In addition, as shown in FIG. 15, the modules 1410a, 1410b, 1411, and 1012 may be integrated into the structure of the band and therefore not visible from the outside of the band.

Figure 16:
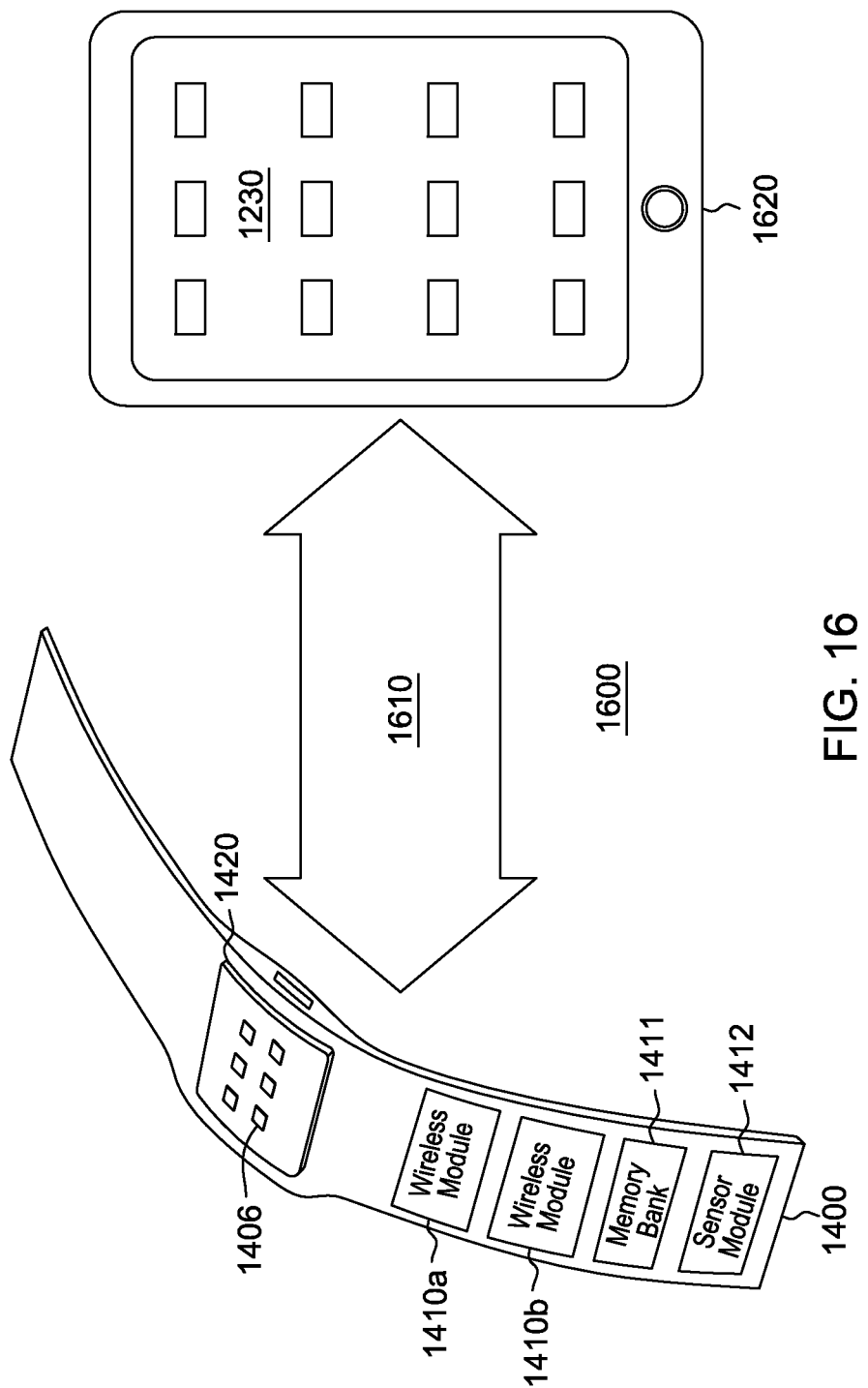
FIG. 16 illustrates the embodiment of FIG. 14 operating in a cloud environment allowing the mobile communication device to link to an external device.

FIG. 16 illustrates the embodiment 1400 operating in a cloud environment 1600. The embodiment 1400 allows mobile communication device 1420 to communicate with an external device 1620. The mobile computing device 1420 can connect directly through a wireless link 1610 or a wired connection (not shown). The mobile computing device 1420 can also link through the wireless modules 1410a and 1410b (e.g., a WLAN module, a WWAN module) and the wireless link 1610 to the external device 1620. The wireless link 1610 may be made using WiFi, SuperWiFi, WHDMI, Bluetooth, NFC type protocols, 3G/4G, or the like. The external device 1620 can be almost any type of display device such as an iPad®, iPhone®, PC tablet, Android® based tablet, TouchPad, Nexus 7®, Slate®, smart TV, display for a projection device or the like. The band system described herein allows a user of the band to easily display information stored in the memory bank 1411 on the band to an external device 1620. Therefore, the operator of the band does not have to carry around a large display but rather can mate (usually wirelessly) with almost any type of much larger display to share information stored in the memory banks of the band including text, audio and video materials. In alternative embodiments, the computing device may not have a screen at all and the band may be designed to provide the functionalities of a mobile computing device but without a display screen at all. The band (whether there is a mobile computing device mounted therein or not) is configured to mate with whichever display is readily available. Embodiments 1100, 1200, 1300, 1700, 1800, 1900, 2000, 2100, 2200, and 2300 discussed herein are also configured to mate with an external device.

FIG. 17 illustrates an embodiment 1700 of the PCCC which has a screen 1700b mounted on a structure such as band 1700a. Examples of the band 1700a include a bracelet or sweatband. The screen 1700b may be flexible and cover less than the entire band in a range approximately 25% to 50% of the band or 50% to 75% of the band. The screen 1700b may be an OLED, LED, LCD, Mirasol®, E Ink or the like. In alternative embodiments, the screen 1700b may include an embedded digitizer for drawing, writing and taking notes and be pen input sensitive. Embodiment 1700 provides a personal cloud to the user and access to wireless networks (such as 3G, 4G, WiFi, SuperWiFi, and similar wireless technologies). The structure 1700 may be a band 1700a made of waterproof material and manufactured by injection molding. Electronics components in the band such as controllers, memory modules, batteries, and the like may be entirely covered by the structural material. The band 1700a may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. In alternative embodiments the structure 1700 may be made of any material (hard and/or soft) that makes the embodiment 1700 lightweight but durable and resilient such as plastic, silicone, ceramic, fabric, leather, steel, aluminum, fiberglass, titanium, Kevlar, and/or rubber. The band 1700a may be substantially circular or substantially oblong in shape and be capable of being wrapped around the hand, wrist, forearm, bicep, head, or leg of the wearer or around the wearers' clothing such as a hat (or helmet). The band may have some type of clasping device (e.g, Velcro, metal clasp, etc.) mounted on each of the ends of the band for attachment. Wireless charging circuitry may extend out from both sides of screen 1700b. The wireless charging circuitry can provide both power and serve as a data link. The wireless charging circuitry may be ribbon cable so that it flexibly bends with the band. Wireless charging circuitry may be internal to the band 1700a and extend along substantially the length of the band. The wireless charging circuitry may be wireless and have memory modules. The wireless charging circuitry may be configured to transfer power from at least one, several or all of the of the modules to screen 1700b (or an attached mobile computing device) or may transfer power from the screen 1700b (or an attached mobile computing device) to at least one, several or all of the modules. Similar to synchronization button 230, the band may also have an input configured to direct the plurality of electronic components to receive synchronization information from a wireless network. The band 1700a may contain an antenna. A wireless charging unit may be connected to the wireless charging circuitry and may operate by magnetic resonance, inductive charging, or power over RF or similar wireless charging methods to charge the screen 1700b or a nearby mobile computing device. Along with the wireless charging unit there may be a battery located in the band 1700a and in connection with the wireless charging unit and the wireless charging circuitry. The band 1700a may include data ports providing outside connections to the band 1700a and screen 1700b. The data ports may be microUSB, HDMI, NV inputs or the like and are linked to both the screen 1700b and over wireless charging circuitry to the modules. One port may be a charging port to provide power to the wireless charging unit and/or a battery and ultimately to the screen 1700b and the electronic components in the band 1700a. Electrically connected to the screen 1700b may be a plurality of wireless modules. One wireless module may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be in communication with the wireless modems, the band is therefore configured to allow for simultaneous connection of the mobile communication device with the memory bank and through the wireless modem to an external network. There may also be a module (similar to module 220) that may be sensory module and may contain a sensor chip which can detect biometric inputs such as finger prints, eye movement, face shape and the like.

FIGS. 18A and 18B illustrate an embodiment 1800 of the PCCC which has a wallet structure which is similar in structure (albeit smaller) to the case 200 as shown in FIG. 2A with a first wallet panel 1800a and a second wallet panel 1800b. As shown in FIG. 18A, screen 1800c may be embedded or mounted on the outside of the first wallet panel 1800. The screen 1800c may be flexible and cover in a range between either approximately half the entire surface or the approximately the entire surface of first wallet panel 1800a. The screen 1800c may be an OLED, LED, LCD, Mirasol®, E Ink or the like. The screen 1800c could have an embedded digitizer for drawing, writing and taking notes and be pen input sensitive. FIG. 18B shows the wallet 1800 in an open position. As discussed with regard to previous embodiments above, wallet 1800 provides a personal cloud to the user and access to wireless networks (such as 3G, 4G, WiFi, SuperWiFi, and similar wireless technologies). The wallet 1800 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the wallet 1800 such as controllers, memory modules, batteries, and the like may be entirely covered by the structural material. The structure 1800 may be made of leather and/or waterproof material. In alternative embodiments the structure 1800 may be made of any material (hard and/or soft) that makes the embodiment 1800 lightweight but durable and resilient such as plastic, silicone, ceramic, fabric, leather, steel, aluminum, fiberglass, titanium, Kevlar, and/or rubber. The wallet 1800 may be approximately rectangular in shape. Wireless charging circuitry may extend out from the screen 1800c. The wireless charging circuitry can provide both power and serve as a data link. The wireless charging circuitry may be ribbon cable so that it flexibly bends with the wallet. Wireless charging circuitry may be internal to the wallet and extend along substantially the length of the wallet in both the first panel 1800a and the second panel 1800b. The wireless charging circuitry may operate wirelessly and have a plurality of modules. The wireless charging circuitry may be configured to transfer power from at least one, several or all of the of the modules to screen 1800c or may transfer power from the screen 1800c to at least one, several or all of the modules. The wireless charging circuitry may also attach (e.g., through a USB port) to a mobile computing device to provide power to or receive power from the mobile computing device. Similar to synchronization button 230, the wallet 1800 may also have an input configured to direct the plurality of electronic components to receive synchronization information from a wireless network. The wallet 1800 may further contain an antenna. A wireless charging unit may be connected to wireless charging circuitry and may operate by magnetic resonance, inductive charging, or power over RF or similar wireless charging methods to charge the screen 1800c or provide power to or receive power from a nearby mobile computing device and/or modules (e.g., power modules) in the wallet 1800. Along with the wireless charging unit there may be a battery located in the wallet 1800 and in connection with the wireless charging unit and the wireless charging circuitry. The wallet 1800 may include data ports providing outside connections to the wallet 1800 and screen 1800c. The data ports may be microUSB, HDMI, NV inputs or the like and are linked to both the screen 1800c and over wireless charging circuitry to the modules. One port may be a charging port to provide power to the wireless charging unit, a battery, screen 1800c, the electronic components in the wallet 1800 and/or an attached (or detached) mobile computing device. Electrically connected to the screen 1800c may be wireless modules. One wireless module may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be communication with the wireless modems, the wallet 1800 is therefore configured to allow for simultaneous connection of the mobile communication device with the memory bank and through the wireless modem to a network. There may also be a module (similar to module 220) which may be a sensory module and may contain a sensor chip which can detect biometric inputs such as finger prints, eye movement, face shape and the like.

FIGS. 19A and 19B illustrate an embodiment 1900 of the PCCC which also has a wallet structure with a first wallet panel 1900a and a second wallet panel 1900b. Embodiment 1900 is constructed and functions in the same manner as embodiment 1800 except for the absence of a screen.

FIGS. 20A and 20B illustrate an embodiment 2000 of the PCCC which has a collar structure with a first collar panel 2000a and a second collar panel 2000b. As discussed with regard to previous embodiments above, collar 2000 provides a personal cloud to the user and access to wireless networks (such as 3G, 4G, WiFi, SuperWiFi, and similar wireless technologies). The structure 2000 may be made of clothe and/or waterproof material. The collar 2000 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the collar 2000 such as controllers, memory modules, batteries, and the like may be entirely covered by the structural material. In alternative embodiments the structure 2000 may be made of any material (hard and/or soft) that makes the embodiment 2000 lightweight but durable and resilient such as plastic, silicone, ceramic, fabric, leather, steel, aluminum, fiberglass, titanium, Kevlar, and/or rubber. The collar 2000 may be rectangular or trapezoidal in shape. Wireless charging circuitry may extend throughout the first collar panel 2000a and second collar panel 2000b. The wireless charging circuitry can provide both power and serve as a data link. The wireless charging circuitry may be ribbon cable so that it flexibly bends with the collar. Wireless charging circuitry may be internal to the collar and extend along substantially the length of the collar in both the first panel 2000a and the second panel 2000b and electrically connect the two panels. The wireless charging circuitry may be wireless and have a plurality of modules. The wireless charging circuitry may be configured to transfer power from at least one, several or all of the of the modules. A mobile wireless device may be configured to attach to the collar 2000 and receive power from or provide power to the wireless charging circuitry. Similar to synchronization button 230, the collar 2000 may also have an input configured to direct the plurality of electronic components to receive synchronization information from a wireless network. The collar 2000 may further contain an antenna. A wireless charging unit may be connected to wireless charging circuitry and may operate by magnetic resonance, inductive charging, or power over RF or similar wireless charging methods to provide power to or receive power from a mobile computing device and/or the modules (e.g., power modules) in the collar 2000. Along with the wireless charging unit there may be a battery located in the collar 2000 and in connection with the wireless charging unit and the wireless charging circuitry. The collar 2000 may include data ports providing outside connections to the collar 2000. The data ports may be microUSB, HDMI, A/V inputs or the like and are linked wireless charging circuitry to the modules. One port may be a charging port to provide power to the wireless charging unit, a battery, the electronic components in the collar 2000 and/or an attached (or nearby detached) mobile computing device. The collar 2000 may include a wireless module which may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be communication with the wireless modems, the band is therefore configured to allow for simultaneous connection of the mobile communication device with the memory bank and through the wireless modem to a network. There may also be a module (similar to module 220) may be sensory module and may contain a sensor chip which can detect biometric inputs such as finger prints, eye movement, face shape and the like.

FIG. 21 illustrates an embodiment 2100 of the PCCC which has a key chain (or fob) shape with a key chain panel 2100a. As discussed with regard to previous embodiments above, key chain 2100 provides a personal cloud to the user and access to wireless networks (such as 3G, 4G, WiFi, SuperWiFi, and similar wireless technologies). The structure 2100 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the band such as controllers, memory modules, batteries, and the like may be entirely covered by the structural material. The structure 2100 may be made of waterproof material. In alternative embodiments the structure 2100 may be made of any material (hard and/or soft) that makes the embodiment 2100 lightweight but durable and resilient such as plastic, silicone, ceramic, fabric, leather, steel, aluminum, fiberglass, titanium, Kevlar, and/or rubber. The key chain 2100 may be substantially rectangular, substantially cubic or substantially circular in shape. Wireless charging circuitry may extend throughout the key chain panel 2100a. The wireless charging circuitry can provide both power and serve as a data link. The wireless charging circuitry may be a ribbon cable. Wireless charging circuitry may be internal to the key chain 2100 and extend along substantially the length of the key chain panel 2100a. The wireless charging circuitry may be wireless and have a plurality of modules. The wireless charging circuitry may be configured to transfer power from at least one, several or all of the modules. A mobile wireless device may be configured to attach to the key chain panel 2100a and receive from or provide power to the wireless charging circuitry. Similar to synchronization button 230, the key chain 2100 may also have an input configured to direct the plurality of electronic components to receive synchronization information from a wireless network. The key chain 2100 may further include an antenna. A wireless charging unit may be connected to wireless charging circuitry and may operate by magnetic resonance, inductive charging, or power over RF or similar wireless charging methods to provide power to or receive power from a nearby mobile device and/or modules (e.g., power modules) in the key chain 2100. Along with the wireless charging unit there may be a battery located in the key chain 2100 and in connection with the wireless charging unit and the wireless charging circuitry. The key chain may include data ports providing outside connections to the key chain 2100. The data ports may be microUSB, HDMI, NV inputs or the like and are linked wireless charging circuitry to the modules. One port may be a charging port to provide power to the wireless charging unit, a battery, the electronic components in the key chain 2100 and/or an attached (or nearby non-attached) mobile device. The key chain 2100 may include a wireless module which may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be in communication with the wireless modems, the band is therefore configured to allow for simultaneous connection of the mobile computing device with the memory bank and through the wireless modem to a network. There may also be a module (similar to module 220) may be sensory module and may contain a sensor chip which can detect biometric inputs such as finger prints, eye movement, face shape and the like.

FIG. 22 illustrates an embodiment 2200 of the PCCC which has a tie shape structure with a tie panel 2200a. As discussed with regard to previous embodiments above, tie 2200 provides a personal cloud to the user and access to wireless networks (such as 3G, 4G, WiFi, SuperWiFi, and similar wireless technologies). The structure 2200 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the tie such as controllers, memory modules, batteries, and the like may be entirely covered by the structural material. The structure 2200 may be made of clothe and/or waterproof material. In alternative embodiments the structure 2200 may be made of any material (hard and/or soft) that makes the embodiment 2200 lightweight but durable and resilient such as plastic, silicone, ceramic, fabric, leather, steel, aluminum, fiberglass, titanium, Kevlar, and/or rubber. Wireless charging circuitry may extend throughout the tie panel 2200a. The wireless charging circuitry can provide both power and serve as a data link. The wireless charging circuitry may be a flexible, ribbon cable. Wireless charging circuitry may be internal to the tie 2200 and extend along substantially the length of the tie panel 2200a. The wireless charging circuitry may be wireless and have a plurality of modules. The wireless charging circuitry may be configured to transfer power from at least one, several or all of the of the modules or an attached (e.g, by USB) mobile computing device. Similar to synchronization button 230, the tie 2200 may also have an input configured to direct the plurality of electronic components to receive synchronization information from a wireless network. The tie 2200 may further contain an antenna. Wireless charging unit may be connected to wireless charging circuitry and may operate by magnetic resonance, inductive charging, or power over RF or similar wireless charging methods to provide power to or receive power from a nearby mobile computing device and/or modules (e.g., power modules) in the tie 2200. Along with the wireless charging unit there may be a battery located in the tie 2200 and in connection with the wireless charging unit and the wireless charging circuitry. The tie 2200 may include data ports providing outside connections to the tie 2200. The data ports may be microUSB, HDMI, A/V inputs or the like and are linked wireless charging circuitry to the modules. One port may be a charging port to provide power to the wireless charging unit, a battery, the electronic components in the tie 2200 and/or an attached mobile computing device. The tie 2200 may include a wireless module which may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be in communication with the wireless modems, the tie is therefore configured to allow for simultaneous connection of the mobile communication device with the memory bank and through the wireless modem to a network. There may also be a module (similar to module 220) which may be sensory module and may contain a sensor chip which can detect biometric inputs such as finger prints, eye movement, face shape and the like.

Figure 23:
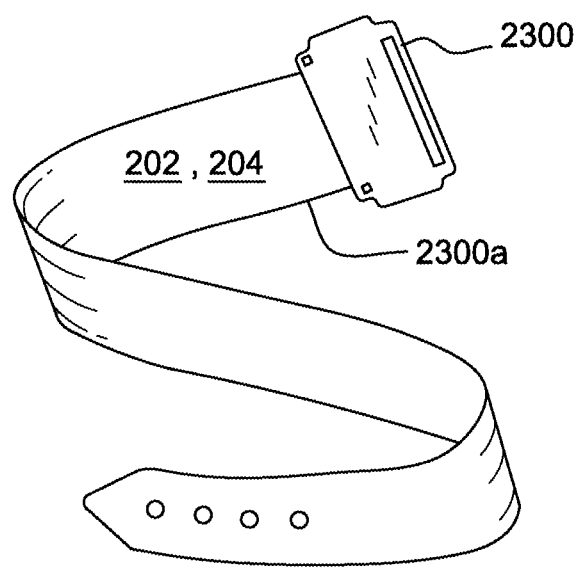
FIG. 23 illustrates an embodiment of the PCCC which has a belt shape.

FIG. 23 illustrates an embodiment 2300 of the PCCC which has a belt shape structure with a belt panel 2300a. As discussed with regard to previous embodiments above, belt 2300 provides a personal cloud to the user and access to wireless networks (such as 3G, 4G, WiFi, SuperWiFi, and similar wireless technologies). The structure 2300 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the belt 2300 such as controllers, memory modules, batteries, and the like may be entirely covered by the structural material. The structure 2300 may be made of clothe, leather and/or waterproof material. In alternative embodiments the structure 2300 may be made of any material (hard and/or soft) that makes the embodiment 2300 lightweight but durable and resilient such as plastic, silicone, ceramic, fabric, leather, steel, aluminum, fiberglass, titanium, Kevlar, and/or rubber. The belt 2300 may be rectangular in shape. Wireless charging circuitry may extend throughout the belt panel 2300a. The wireless charging circuitry can provide both power and serve as a data link. The wireless charging circuitry may be a flexible, ribbon cable. Wireless charging circuitry may be internal to the belt 2300 and extend along substantially the length of the belt panel 2300a. The wireless charging circuitry may be wireless and have a plurality of modules. The wireless charging circuitry may be configured to transfer power from at least one, several or all of the of the modules or to an attached (or detached) mobile computing device. Similar to synchronization button 230, the belt 2300 may also have an input configured to direct the plurality of electronic components to receive synchronization information from a wireless network. The belt 2300 may further contain an antenna. A wireless charging unit may be connected to the wireless charging circuitry and may operate by magnetic resonance, inductive charging, or power over RF or similar wireless charging methods to provide power to or receive power from a nearby mobile computing device and/or modules (e.g., power modules) on the belt 2300. Along with the wireless charging unit there may be a battery located in the belt 2300 and in connection with the wireless charging unit and the wireless charging circuitry. The belt 2300 may include data ports providing outside connections to the belt 2300. The data ports may be microUSB, HDMI, NV inputs or the like and are linked wireless charging circuitry to the modules. One port may be a charging port to provide power to the wireless charging unit, a battery, the electronic components in the belt 2300 and/or an attached mobile computing device. The belt 2300 may include a wireless module which may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be communication with the wireless modems, the band is therefore configured to allow for simultaneous connection of the mobile communication device with the memory bank and through the wireless modem to a network. There may also be a module (similar to module 220) which may be sensory module and may contain a sensor chip which can detect biometric inputs such as finger prints, eye movement, face shape and the like.

In this disclosure, devices that are described as in "communication" with each other or "coupled" to each other need not be in continuous communication with each other or in direct physical contact, unless expressly specified otherwise. On the contrary, such devices need only transmit to each other as necessary or desirable, and may actually refrain from exchanging data most of the time. For example, a machine in communication with or coupled with another machine via the Internet may not transmit data to the other machine for long period of time (e.g. weeks at a time). In addition, devices that are in communication with or coupled with each other may communicate directly or indirectly through one or more intermediaries.

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Moreover, the illustration of a process by its depiction in a drawing does not imply that the illustrated process is exclusive of other variations and modifications thereto, does not imply that the illustrated process or any of its steps are necessary to the embodiment(s), and does not imply that the illustrated process is preferred.

The foregoing description and embodiments have been presented for purposes of illustration and description and are not intended to be exhaustive or to limit the embodiments in any sense to the precise form disclosed. Also, many modifications and variations are possible in light of the above teaching. The embodiments were chosen and described to best explain the principles of the disclosure and its practical application to thereby enable others skilled in the art to best use the various embodiments disclosed herein and with various modifications suited to the particular use contemplated. The actual scope of the invention is to be defined by the following claims.

The invention claimed is:

1. A structure configured to connect to a mobile computing device, the structure comprising:
   a cavity capable of holding the mobile computing device;
   a power source located exterior to and coupled to the cavity and to a plurality of modules located in the structure and capable of providing power to the plurality of modules; and
   wherein the plurality of modules include at least one wireless modem which allows the case to wirelessly transmit and receive signals from other electronic devices.

2. The structure of claim 1 wherein the at least one wireless modem is a WLAN modem.

3. The structure of claim 1 wherein the at least one wireless modem is a WWAN modem.

4. The structure of claim 1, further comprising:
   an antenna capable of coupling the mobile computing device to a wireless network.

5. The structure of claim 1, further comprising:
   a memory bank capable of being coupled to the mobile computing device; and
   wherein the memory bank includes a plurality of memory modules.

6. The structure of claim 5, wherein the plurality of memory modules are capable of backing up information stored on the mobile computing device.

7. The structure of claim 5, wherein the memory bank is wirelessly coupled to the mobile computing device.

8. The structure of claim 1, further comprising:
   a circuit embedded in the structure which is capable of forming a data link between the mobile computing device and a plurality of modules located in the structure.

9. The structure of claim 1, further comprising:
   a charging unit located in the cavity and capable of wirelessly charging the mobile computing device and receiving charge from the mobile computing device.

10. The structure of claim 1, further comprising:
    a sensor chip configured to detect biometric inputs selected from the group consisting of: fingerprints, eye movement, and face shape; and
    wherein the sensor chip provides a security function to deny unauthorized access to a plurality of components in the structure.

11. The structure of claim 1, wherein the structure is in the shape of a band.

12. The structure of claim 1, wherein the structure is in the shape of a wallet.

13. The structure of claim 1, wherein the structure is in the shape of a key chain.

14. The structure of claim 1, wherein the structure is in the shape of a belt.

15. The structure of claim 1, wherein the structure is in the shape of a collar.

16. The structure of claim 1, wherein the structure is in the shape of a tie.

17. The structure of claim 1, wherein at least one of the plurality of modules is a sensor module.

18. The structure of claim 17, wherein the sensor is used for medical purposes.

19. A case for a mobile communication device, the case comprising:

a first panel and a second panel capable of forming a compartment for the mobile computing device;

said first panel having a screen;

a power source attached to the second panel and connected to a plurality of modules located on at least one of the first and second panels and capable of providing power to the plurality of modules; and wherein the plurality of modules include a WWAN modem and a WLAN modem which allow the case to wirelessly transmit and receive signals from other electronic devices.

20. The case of claim 19, wherein the screen is selected from a group consisting of: OLED, LED, LCD, Mirasol®, and E Ink.

21. The case of claim 19, wherein the screen includes a digitizer.

22. The case of claim 21, further comprising:

a pressure sensitive pen for inputting into the screen.

* * * * *